United States Patent [19]

Moro et al.

[11] 4,272,518

[45] Jun. 9, 1981

[54] PLASTIC WOUND BANDAGE

[76] Inventors: Daniel G. Moro, 7 Carriage Ct., Randolph, N.J. 07801; Gary A. Griffin, 2 Pilgrim Run, East Brunswick, N.J. 08816; Mark J. D'Andrea, 70 C Zion Montgomery Rd., Neshanic Station, N.J. 08553

[21] Appl. No.: 56,183

[22] Filed: Jul. 10, 1979

[51] Int. Cl.$^3$ .............................................. A61K 31/78
[52] U.S. Cl. .................................. 424/81; 424/78; 424/177; 424/227; 424/229; 424/230; 424/243; 424/263; 424/271; 424/310; 424/324; 424/329; 424/339; 424/347
[58] Field of Search .................................. 424/78, 81

[56] References Cited

U.S. PATENT DOCUMENTS

| | | | |
|---|---|---|---|
| 3,575,946 | 4/1971 | Chromecek et al. | 260/86.1 X |
| 3,577,516 | 5/1971 | Gould et al. | 424/46 |
| 3,618,213 | 11/1971 | Shepherd et al. | 424/81 X |
| 3,868,447 | 2/1975 | Kliment | 424/81 |
| 3,963,685 | 6/1976 | Abrahams | 424/81 X |

*Primary Examiner*—Leonard Schenkman
*Attorney, Agent, or Firm*—Cushman, Darby & Cushman

[57] ABSTRACT

There is provided a composition and a process of treating a wound, especially burned tissue surface comprising applying to the wound a settable, non-toxic paste comprising a particulate, hydrophilic, water-swellable polymer and an inert, water-miscible organic liquid having a boiling point above about 120° C. capable of forming a paste therewith, said paste having a setting time of up to an hour and a working time sufficient to apply to the paste to the burned tissue surface, the polymer of said paste in set condition being water-insoluble.

34 Claims, No Drawings

PLASTIC WOUND BANDAGE

BACKGROUND OF THE INVENTION

The invention relates to improvements in the treatment of wounds.

Thermal injuries require a unique combination of therapy and dressing as the physiologic functions of the skin are absent or, at best, materially impaired. Various proposals have been made to provide a film or protective barrier to the involved lesion including generally providing polymer compositions capable of forming in situ pinhole-free, mechanically strong, translucent or transparent or opaque, non-tacky dressing. Typically, such procedures include application of a normally liquid organic vehicle to the affected area followed by or simultaneously with a powdery hydrophilic polymer. The bandage or dressing thus being formed is a plastic film of hydrophilic polymer solvated into the liquid organic vehicle. Notwithstanding clinical acceptance of such dressing and technique, clinicians reported that the film set-up time, i.e., that amount of time from when the organic vehicle and hydrophilic polymer come into contact on the burned tissue until the desired film burn dressing is achieved, was in many cases excessive, oftentimes taking longer than one hour. The set-up time is inconvenient, often painful, to the patient who must maintain the treated area in immobile condition. This is particularly true in instances of larger burn wounds.

Furthermore it is old to form a burn dressing in situ by spraying alternating layers of an inert, normally liquid, organic vehicle (hereinafter oftentimes referred to as "solvent" for convenience), e.g., polyethylene glycol 400, and particulate hydrophilic polymer, e.g., three dimensional polymer of 2-hydroxyethyl methacrylate. Apparently solvation or plasticization occurs and with time, the two components (polymer solvated in the solvent) "set" yielding a plasticized, integral, non-tacky, occlusive dressing of the order of several tenths mm., e.g., 0.3 to 0.7 mm. thick (dependent on how many alternating layers are applied). Spray delivery of the two components is achieved using compressed gas sources (nitrogen tank, compressor, etc.) and requires additional equipment such as glass dispensers, tubing, cut-off assemblies, etc., to be used. This spraying technique, when done properly by trained personnel, yields films of excellent quality. However, this application method is very tedious and cumbersome and the quality of the resulting films are totally dependent on the technique of application and quantity of the components being sprayed.

THE INVENTION

It has now been found that the aforedescribed disadvantages can be overcome by applying to the wound, especially burned tissue surface (usually a second, third or fourth degree burn surface) a novel settable paste comprising water-insoluble, water-swellable, non-toxic hydrophilic polymer and an inert, normally-liquid organic vehicle having a relatively high boiling point. The novel paste possesses a setting time period no greater than about one hour, and a working time period which is sufficient to permit an operator (e.g., clinician, nurse, doctor) to apply the novel paste to the wound and thereby obtaining an integral, homogeneous, non-tacky occlusive film dressing. The polymer component of the paste when in set condition is water-insoluble. The preferred polymer is three dimensional 2-hydroxyethyl methacrylate polymer and the preferred solvent is polyethylene glycol of 400–800 molecular weight.

It is deemed advisable at this time to set forth certain definitions which will facilitate in understanding applicants' contribution to the art.

The term "hardening time", as used herein, is the period of time during which the novel paste (in the mixing vessel) is in a settable and usable state. After the hardening time period is exceeded (in the mixing vessel) the paste "hardens" and "sets"; wound dressings therefrom are either non-attainable or very poor in characteristics. One can liken such hardened or set pastes with a mixture of plaster of paris and water which has remained in the mixing vessel beyond its settable period.

The term "setting time", as used herein, is the period of time required commencing upon application of the novel paste to the body surface, to form a non-tacky, occlusive film (dressing) on such surface.

The term "working time", as used herein, is the maximum period of time the novel paste can be contained in the mixing vessel and still be applied to a body surface to obtain a non-tacky occlusive film (dressing) on such surface.

The paste system can be applied to dry or wet body surfaces. In desirable embodiments of the invention it has been observed that the setting time of preferred novel pastes can be decreased to a period of approximately 30 minutes by applying the paste to a wet body surface without any loss of adhesion of the resulting integral, homogeneous, non-tacky, occlusive film. This is indeed an unexpected and beneficial advantage since a major use contemplated herein is application of the paste to burn tissue characterized by exudate.

Advantages which accrue by the practice of the invention include the following:

1. Application is simple, convenient and hardware free.
2. Applying a paste does not require any additional expertise by the hospital personnel since they currently treat burn victims with creams that are applied with a tongue depressor. Set-up time is less than one hour, e.g., 25–42 minutes.
3. The patient can be covered rapidly and effectively without extraordinary diligence by the hospital personnel because the paste is self leveling.
4. Exact quantities of hydrophilic polymer powder and solvent at the appropriate ratio are delivered with the paste technique. The quality of the resulting film is not operator dependent and, therefore, the chance for film failure is dramatically reduced.
5. Minimum preparation is required before application.
6. No dusting (due to polymer) results using this mode of application.
7. The paste, when applied to a wet surface, sets into a film faster and adheres as well as when applied to a dry surface.
8. This burn dressing application system can be used anywhere for emergency treatment of burns because it is not dependent on compressed gas sources or electrical outlets.
9. Working time is adequate, e.g., 1 to 20 minutes.

Desirably, the hydrophilic polymer has a high purity level (low level of residual monomer to prevent toxic or allegenic reaction). Also, the polymer should be water-insoluble to prevent excess tackiness caused by perspiration, liquid oozing from the wound, etc.

The molecular weight of the hydrophilic polymer desirably is of at least about 50,000 and preferably above about 250,000 and upwards to several million. Molecular weights over the entire range and even outside these limits may be tolerated providing the hydrophilic polymers meet the characteristics noted in this specification. Hydrophilic polymer in particulate form is employed in the preparation of the novel pastes. Desirably, the polymer is micropulverized to particles of a dimension smaller than 50 mesh, preferably below 100 mesh (Tyler sieve). In one desirable embodiment, the bulk density of the particulate hydrophilic powder is at least about 0.6 gram/cc, and preferably at least about 0.7 gram/cc. Polymers of 2-hydroxyethyl methacrylate in the 100 to 375 mesh range are particularly suitable in the practice of preferred aspects of the invention.

The water-insoluble, water-swellable hydrophilic polymer should be capable of forming with the solvent a settable gel. The solvents contemplated herein are inert, non-toxic, normally-liquid, water-miscible organic liquids as exemplified by water-miscible polar compounds including the glycols such as ethylene glycol, propylene glycol, dipropylene glycol, butanediol-1,3, butanediol-1,4, hexanediol-2,5, 2-methyl-2,4-pentanediol, heptanediol-2,4, 2-ethyl-1,3-hexanediol, diethylene glycol, triethylene glycol, tetraethylene glycols, and the higher polyethylene glycols and other water-soluble oxyalkylene homopolymers and copolymers having a molecular weight up to 2000, and higher, desirably up to 1600, e.g., hydroxy-terminated polymers of ethylene oxide having average molecular weights of 200–1000, the water-soluble oxyethyleneoxypropylene polyol (especially glycol) polymers having molecular weights up to about 1500, desirably up to about 1000, propylene glycol monoethyl ether, monoacetin, glycerine, tri(hydroxyethyl) citrate, ethylene glycol monomethyl ether, ethylene glycol monoethyl ether, di(hydroxypropyl) oxalate, hydroxypropyl acetate, glyceryl triacetate, glyceryl tributyrate, liquid sorbitol ethylene oxide adducts, liquid glycerine ethylene oxide adducts, diethylene glycol monomethyl ether, diethylene glycol monoethyl ether, and ethylene glycol diacetate.

The organic liquids have boiling points above about 120° C., and preferably above about 200° C. The organic liquids vehicles which are particularly useful in forming non-tacky plastisol films when combined with the particulate hydrophilic polymer are the water-miscible oxyalkylene polymers, e.g., the polyalkylene glycols, especially those characterized by: (i) a plurality of oxyethylene ($-OCH_2-CH_2-$) units in the molecule, and (ii) a boiling point above about 200° C.

The proportion of polymer to organic liquid will be governed, to a significant extent, by variables such as the hydrophilic polymer of choice, the particle size of the polymer, the molecular weight of the polymer, the organic liquid of choice, the molecular weight of the organic liquid, the particular hardening time, setting time, and/or working time which the operator or clinician desires, and other factors. As will be apparent from a consideration of the working Examples, the setting period exceeds the working time period, and mixing the components together to obtain a uniform paste is relatively easy to accomplish, e.g., use of a tongue depressor for 60 seconds, followed by application to a body surface (wound). Taking into account the above factors, one skilled in the art can readily determine the optimum amount of particulate hydrophilic polymer relative to solvent which is necessary to yield a paste possessing a setting time of up to about 1 hour, preferably less than one hour, e.g., less than 45–50 minutes, and a working time which is sufficient to allow an operator to apply the paste to the body surface and still obtain an integral, homogeneous, non-tacky occlusive film of sufficient mechanical strength and adhesiveness on the body surface for several days, e.g., one or two days to a week. In the practice of preferred aspects of the invention novel pastes are prepared by using polymer to solvent ratios (by weight) of from above about 0.8:1 to about 1.4:1, preferably from about 0.85:1 to below about 1.4:1, preferably still from about 0.85:1 to about 1.25:1, and most preferably from above about 0.85:1 to below about 1.25:1. The above ranges are particularly suitable in the preparation of burn dressing films comprised of cross-linked 2-hydroxyethyl methacrylate polymers and polyethylene glycol of 200–1600 molecular weight, especially 200–1000 mol weight, and from a commercial viewpoint 400 mol weight.

By the practice of the invention there are formed translucent or transparent or opaque, non-tacky, homogeneous, integral, non-toxic, non-stinging, occlusive films or body dressings of good mechanical properties and integrity. Such dressings have proved particularly useful in the treatment of wounds such as burn trauma, e.g., second, third and fourth degree burns, especially the difficult to treat third and fourth degree burns.

The novel paste can be applied to the burn surface by any convenient method, e.g., it can be troweled on by a tongue depressor or a spatula. There results a plastic film (which on a burn victim has been oftentimes referred to herein as a burn bandage or burn dressing) of hydrophilic polymer gel solvated into the liquid component. The finished bandage can be removed by soaking in water. The film can be considered a plastisol, the external surface of which appears dry to the touch, i.e., without excess liquid component. The film can remain in place as long as required by the progress of the healing process (up to a week or more). The dressing can be readily removed by bathing or washing with water, or by pulling.

The thickness of the in situ dressing can be adequately controlled by monitoring the quantities of paste applied.

As the hydrophilic polymeric component useful in the practice of the invention there is used a hydrophilic, water-insoluble, water-swellable, generally at least slightly crosslinked, non-toxic, particulate solid. Preferred classes of monomers useful in the preparation of the hydrophilic polymer component are the hydroxyalkyl 2-alkenoates such as the hydroxy($C_2$–$C_4$alkyl) methacrylates and the hydroxy($C_2$–$C_4$alkyl) acrylates; the hydroxy($C_2$–$C_4$alkoxy$C_2$–$C_4$alkyl) alkenoates, e.g., 2-hydroxyethoxyethyl acrylate and methacrylate; the alkoxy($C_2$–$C_4$alkoxy$C_2$–$C_4$alkyl) alkenoates, e.g., methoxyethoxyethyl acrylate and methacrylate; the N-vinylpyrrolidones including the mono- and di-($C_1$–$C_4$alkyl)-N-vinylpyrrolidones; the 2-alkenamides including the N-($C_1$–$C_4$alkyl)-2-alkenamides and $N_1$N-di($C_1$–$C_4$alkyl)-2-alkenamides such as the N-($C_1$–$C_4$alkyl)acrylamides, the N-($C_1$–$C_4$alkyl)-methacrylamides, the $N_1$N-di($C_1$–$C_4$alkyl)acrylamides, and $N_1$N-di($C_1$–$C_4$alkyl)methacrylamides; the vicinal-epoxyalkyl 2-alkenoates including the vicinal-epoxy($C_1$–$C_4$alkyl) methacrylates, and the vicinal-epoxy($C_1$–$C_4$alkyl) acrylates; with or without other monomers or modifiers such as the alkyl alkanoates, e.g., methyl butyrate, butyl acetate, etc.; the dialkylaminalkyl 2-alkenoates, e.g., diethylaminoethyl methacrylate; the vinylpyridines; the lower alkoxy(lower alkyl) methacrylates, e.g., ethoxyethyl methacrylate; and mixtures of the illustrative foregoing compounds.

Preferred monomers include, by way of examples, 2-hydroxyethyl acrylate, 2-hydroxyethyl methacrylate, diethylene glycol monoacrylate, diethylene glycol monomethacrylate, 2-hydropropyl acrylate, 2-hydroxypropyl methacrylate, 3-hydroxypropyl acrylate, 3-hydroxypropyl methacrylate, dipropylene glycol monomethacrylate, dipropylene glycol monoacrylate, acrylamide, N-methylmethacrylamide, N,N-dimethacrylamide, methylvinylpyrrolidone, glycidyl methacrylate, 2,3-dihydroxypropyl methacrylate, and the like. Most preferred is 2-hydroxyethyl methacrylate.

Desirably, small amounts of cross-linking agent or other ingredient either inherently contained in the monomer and/or added thereto, or other means, e.g., photopolymerization, can be employed to impart a three-dimensional, water-insoluble, structure to the resulting hydrophilic polymer.

Typical examples of crosslinging agents include ethylene glycol diacrylate, ethylene glycol dimethacrylate, 1,4-butylene dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinyl benzene, divinyltoluene, diallyl tartrate, allyl pyruvate, allyl malate, divinyl tartrate, triallyl melamine, N,N'-methylene bisacrylamide, diallyl maleate, divinyl ether, diallyl monoethylene glycol citrate, vinyl allyl citrate, allyl vinyl maleate, diallyl itaconate, ethylene glycol diester of itaconic acid, divinyl sulfone, hexahydro-1, 3,5-triactryltriazine, triallyl phosphite, diallyl ether of benzene phosphonic acid, polyester of maleic anhydride with triethylene glycol, diallyl aconitrate, divinyl citraconate, and diallyl fumarate. Of course, toxic crosslinking agents should not be used.

Also contemplated in the practice of the invention are hydrophilic polymers such as the partially cross-linked polyethyleneimines, the polyoxyethylenes, the vinyl-heterocyclic polymers, e.g., vinylpyrrolidone polymers which are rendered insoluble in water; the hydroxy lower alkyl celluloses, cross-linked or otherwise, and rendered insoluble in water but still retaining their hydrophilicity and solubility in organic solvents such as methanol, e.g., from hydroxyethylcellulose, hydroxypropylcellulose, or carboxymethylcellulose; the partially cross-linked natural polymers such as guar gum, karaya gum, gelatin, e.g., partially cross-linked with formaldehyde or glutaraldehyde and salts of alginic acid which are rendered water insoluble; the polyvinyl alcohols including the various partially hydrolyzed polyvinyl acetates; and the vinyl lower alkyl ether polymers, e.g., vinyl methyl ether and vinyl ethyl ether polymers.

Particularly suitable hydrophilic polymers are those which are characterized by being made from at least 50 mol percent, preferably at least 80 mol percent, of a monomer of the formula:

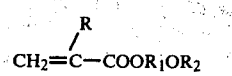

wherein R is hydrogen or methyl; wherein $R_1$ is $C_2$-$C_4$ alkylene, e.g., ethylene, propylene or butylene; and wherein $R_2$ is hydrogen or $C_1$-$C_4$ alkyl, or $C_1$-$C_4$ alkoxy $C_1$-$C_4$ alkyl. The resulting hydrophilic polymer will thus be characterized by at least 50 mol percent, preferably at least 80 mol percent, of the following recurring unit:

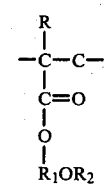

wherein R, $R_1$ and $R_2$ have the aforesaid assigned values.

As an example of a preferred polymer for the present invention is a hydroxyethyl methacrylate polymer prepared by aqueous bulk polymerization using ultra-pure monomers characterized by a very low concentration of impurities conducive to crosslinking reactions, see U.S. Pat. No. 3,963,685. The above polymers can be prepared under "clean conditions" easily purified from residual monomers, and easily reduced to powders of the desired particle size.

It has also been determined that solvent-soluble conventional hydrogel forming polymers, e.g., as in U.S. Pat. No. 3,577,516 to Gould et al., U.S. Pat. No. 3,618,213 to Shepherd, and U.S. Pat. No. 3,575,946 to Chromacek, of sufficiently high molecular weight can be transformed into particulate hydrophilic polymer which is useful in the preparation of the novel pastes. The process disclosed by the patentees involves the dissolution of the polymers in a low boiling point solvent, preferably ethyl alcohol of high purity (at least USP), then filtering the resulting polymer solution through a fritted glass filter (medium porosity). The filtered solution is then cast on clean surfaces and the solvent removed. The then dry film is then collected and ground to appropriate mesh size. The entire disclosure of the aforesaid patents is hereby incorporated by reference.

If a hydrophilic monomer results in a polymer which is water-soluble, e.g., polyacrylamide, it is necessary to employ a sufficient amount, generally up to 50 mol percent, of a copolymerization monomer to render it only water-swellable, rather than water-soluble. Such comonomers include, by way of illustrations, methyl acrylate, ethyl acrylate, propyl acrylate, butyl acrylate, 2-ethylhexyl acrylate, ethyl methacrylate, butyl methacrylate, methoxyethyl acrylate, methoxyethyl methacrylate, and ethoxyethyl methacrylate.

Furthermore, medicinally active ingredients such as germicides, fungicides, antibiotics, analgesics, or the like may be utilized by having the medicinally active ingredient suspended, entrapped in, or admixed with the polymer or in the novel paste. Examples of such medicinally active ingredients include silver sulfadiazine, benzocaine, xylocaine, aspirin, sodium omadine (a derivative of 1-hydroxypyridine-2-thione), hexachlorophene, bacitracin, cortisone, trimethylbenzylammonium chloride, cetyl pyridinium chloride, penicillin, Aureomycin (chlorotetracycline), chloromycetin (chloromphenicol).

The medicinally active ingredients can be incorporated into the dressing by one or more of the following procedures:

A. Incorporation in the hydrophilic polymer powder prior to making the paste by any of the processes described in U.S. Pat. No. 3,576,760, the entire disclosure of which is hereby incorporated by reference.
B. Incorporation with the liquid component of the paste by mixing the solubilizing component with the drug. The drug does not have to be soluble in the liquid.
C. Application of the drug on the wound before or during application of the paste and/or liquid component.
D. Application of the drug on the surface of the occlusive dressing.
E. Mixing into the paste.

Mixtures of hydrophilic polymers and/or mixtures of solvents can be employed provided that the components are compatible in the sense that a homogeneous paste is formed.

The invention can be used to treat wounds, particularly third and fourth degree burns on any skin surface, e.g., on the arms, legs, face, back, head or stomach. The invention is useful not only in treating humans, but also in veterinary medicine, e.g., to treat burns on dogs, cats, sheep, cattle, rabbits, guinea pigs, horses and zoological animals such as lions, tigers, deer, zebra, etc.

The synthetic film comprised of particulate hydrophilic polymer forms on the open surface of the burns and molds itself to the granulating wound.

Unless otherwise indicated, all parts and percentages are by weight. The liquid component in the working example was polyethylene glycol 400 (designated herein as PEG-400).

In the specification and claims there are used certain expressions which are defined below.

As stated previously, the setting time is the period of time required commencing upon application of the novel paste to the body surface, to form an integral, homogeneous, non-tacky, occlusive film. The termination of the setting time period of the resulting film is a subjective test and is recorded when the operator ascertains that such film is occlusive and non-tacky to the touch. A small segment of the film (about 1"×2") is then removed (from the forearm) and is subjected to flexing. The specimen is draped over the middle finger so as to cover the center knuckle and is manually held in place. The film is pressed firmly to the extended finger and the fingers flexed five times in as many seconds. The film is removed and visually inspected for any disturbances of integrity such as tears or stretch marks indicating inelastic stretching. A film is judged to be "excellent" if flexing has produced no tears or signs of inelastic stretching of the film, that is, the resulting film is an integral, homogeneous, non-tacky and occlusive film. Film set time determinations were performed at ambient temperatures of 22°–25° C. and a relative humidity of 72–77%.

The compositions can comprise, consist essentially of, or consist of the materials set forth and the process can comprise, consist essentially of, or consist of the steps with the materials set forth.

The polymer used in the working Examples was prepared as follows.

The particulate hydrophilic polymer was prepared via an aqueous polymerization using 35 parts of 2-hydroxyethyl methacrylate (HEMA) which contained less than 0.04 part of ethylene glycol dimethacrylate. In one container ammonium persulfate (0.0875 part) was dissolved in 32.5 parts of purified water and in a second container sodium metabisulfite (0.0875 part) was dissolved in 32.5 parts of water. The HEMA and both aqueous solutions (redox system) were mixed together in a polyethylene bag which was closed by heat sealing. After 18 hours at room temperature, i.e., about 22° C., the resulting wet polymeric sponge was recovered, wet ground to particles sizes of about 2–4 mm. in diameter, and leached in purified water to yield particulate polymer containing less than 500 ppm (parts per million) of total residuals, e.g., unreacted monomer, redox residue, etc.

The particulate hydrophilic 2-hydroxyethyl methacrylate polymer was then dried, micropulverized and classified. This hydrophilic polymer possessed the following characteristics: soluble in methanol, water-swellable but not water-soluble, bulk density of about 0.7 gm/cc, particle size distribution of 106$\mu$–45$\mu$ with no more than 15 weight percent of the particles being less than 45$\mu$ in diameter, and a reduced viscosity of about 2 dl/g (measured at 0.5 part polymer dissolved in 100 parts of 2-methoxyethanol at about 22° C.; Cannon-Fenske Viscometer 100).

The polymer is hereinafter referred to as polyHEMA powder.

EXAMPLE 1

Into an evaporating dish, 20 g. of PEG-400 were added. Seventeen grams of the polyHEMA powder were added and immediately the components rapidly mixed with a tongue depressor for 60 seconds. The resulting paste was thinly applied with the depressor to an area on the arm approximately 2"×2" and hardening time and setting time determined. The application of the paste was performed on both dry and wet* arm surfaces. The experiment was repeated using 20, 21.5, 23 and 25 grams of the polyHEMA powder and 20 grams of PEG-400. For the addition of 25 g. of the polyHEMA powder to the 20 g. of PEG-400, the components were mixed rapidly for 60 seconds and allowed to stand one minute before application. After all the films set, they were carefully removed via peeling and evaluated for integrity and flexibility as hereinbefore described; see Table I below.

*Water was atomized on the arm for one minute using a compressor and liquid dispenser.

EXAMPLE 2

In vitro films obtained from polyHEMA powder:-PEG-400 ratios of 0.75:1.0, 0.85:1.0, 1.0:1.0, 1.15:1.0, 1.25:1.0, and 1.4:1.0 were prepared by drawing down the paste mixtures on a glass plate with 0.5 mm. borders. The films were allowed to set 24 hours in sealed polyethylene bags, then peeled from the glass, placed on teflon coated foil, and dogbone shapes cut for mechanical testing. The pieces were again sealed in polyethylene bags and conditioned at 72° F. for 24 hours before testing; see Table II below.

EXAMPLE 3

Into an evaporating dish, 20 g of PEG-400 were added. Twenty-three grams of polyHEMA powder were added and immediately the components rapidly mixed with a tongue depressor for 60 seconds. The resulting paste was allowed to stand 10 seconds and applied to a dry area on the arm approximately 5 inches by 3 inches. After the film set, it was carefully removed, evaluated, and actual thicknesses determined over a wide cross-section of the material; see Table III below.

EXAMPLE 4

Into an evaporating dish, 20 g. of PEG-400 were added. Twenty-five grams of polyHEMA powder were added and immediately the components rapidly mixed with a tongue depressor for 60 seconds. The resulting paste was allowed to stand one minute and then applied to different surfaces on a dry arm at various time intervals. The working time and setting time were determined and the resulting films evaluated for quality. The experiment was repeated by adding 10, 15, 17, 21.5, 23 and 30 grams of polyHEMA powder to 20 grams of PEG-400, respectively. The resulting pastes, after mixing, were allowed to stand 10 seconds before application; see Table IV.

RESULTS

Table I below summarizes the results of testing for set-up time performed on various films using different proportions of polyHEMA powder to PEG-400. The results indicate that as the ratio of polyHEMA powder to PEG-400 was increased from 0.85:1 to 1.25:1, the hardening time and setting time decreased. In addition, application of the same paste formulation to a wet surface caused a marked decrease in setting time when compared to application on a dry surface, and no apparent difference in film adhesion ratings were noted.

TABLE I

SETTING TIME
Environmental Conditions
Temperature 72° F.
Relative Humidity 73%

| Paste Composition | Hardening Time in Mixing Vessel (min.) | Surface Applied | Setting time (min.) | Film Rating[a] |
|---|---|---|---|---|
| (Poly HEMA Powder:PEG-400) | | | | |
| 0.85:1.0 | 22 | Dry | 55 | excellent |
| 1.0:1.0 | 18 | Dry | 54 | excellent |
|  | 19 | Wet | 30 | excellent |
| 1.075:1.0 | 17 | Dry | 45 | excellent |
|  | 17 | Wet | 25 | excellent |
| 1.15:1.0 | 15 | Dry | 34 | excellent |
|  | 13 | Wet | 25 | excellent |
| 1.25:1.0 | 13 | Dry | 25 | excellent |

[a] after flex test

Table II below summarizes the results of the physical testing performed on various films prepared via the paste technique using different proportions of polymer powder to PEG-400. Films prepared from the paste technique exhibited a relatively high tensile strength and ultimate elongation and relatively low elastic modulus and tension set (ASTM D 882-73). These are the desirable properties of a viable burn dressing. The tensile strength, ultimate elongation, elastic modulus, and tensile set terms noted briefly below were obtained in accordance with ASTM D 882-73.

*Tensile Strength at Break* is the maximum tensile stress (i.e., applied force per unit of original cross sectional area of a specimen) applied during stretching a specimen to rupture. *Ultimate Elongation* is the maximum extension of a uniform section of a specimen prior to rupture produced by a tensile force applied to the specimen and is expressed as a percentage of the original length of the section.

*Elastic Modulus* is the ratio of stress (nominal) to corresponding strain below the proportional limit of the material and is expressed in force per unit area (i.e., psi).

*Tensile Set at Break* is the extension remaining after a specimen has been stretched to the point of rupture and allowed to retract in a specified manner. It is expressed as a percentage of the original length.

TABLE II

PHYSICAL PROPERTIES
Environmental Conditions
Temperature 72° F.
Relative Humidity 73%

| Specimen Designation | Tensile Strength at Break (psi) | Ultimate Elongation % | Elastic Modulus (psi) | Tensile Set at Break (%) |
|---|---|---|---|---|
| Control (Spray Technique) | 16 | 565 | 349 | 4 |
| 0.75:1.0 (Poly HEMA Powder: PEG-400) | sample did not break | >700 | 975 | sample did not break |
| 0.85:1.0 | 17.8 | 400 | 211 | 4.7 |
| 1.0:1.0 | 36.6 | 420 | 396 | 5.3 |
| 1.15:1.0 | 38.9 | 440 | 440 | 0 |
| 1.25:1.0 | 41.2 | 327 | 262 | 0 |
| 1.40:1.0 | 75.3 | 328 | 602 | 0 |

Table III summarizes the thicknesses determined over a wide cross-section of a film prepared using the paste application technique. A paste formulation of polyHEMA powder to PEG-400 of 1.15:1.0 ratio was applied with a tongue depressor without special application care to a large dry arm surface. From the data in Table III it is apparent that the applied paste flows, self levels, and sets into a film of relatively homogeneous thickness of 0.42 mm (average).

TABLE III

THICKNESS
Environmental Conditions
Temperature 77° F.
Relative Humidity 70%

| Paste Composition | Area Applied on dry arm surface | Film Thickness Variation Determined by Micrometer (mm) |
|---|---|---|
| (PolyHEMA Powder:PEG-400) 1.15:1.0 | 8750 mm² | 0.47, 0.40, 0.40, 0.41, 0.42, 0.41, 0.43, 0.44, 0.39, 0.39, 0.45, 0.49, 0.39, 0.42, 0.39, 0.35, 0.36, 0.40, 0.48, 0.47, 0.45, 0.43, 0.39, 0.42 Average = 0.42 mm |

Table IV below summarizes the results of tests to determine usable working time of various paste systems ranging from polyHEMA powder:PEG-400 ratios of from 0.5:1 to 1.5:1. Usable working times ranged from between 0.75:1 to 0.85:1 (polyHEMA powder:PEG-400) to above 1.25:1 but below 1.5:1 (at 1.5:1 homogeneity was not obtained).

TABLE IV

WORKING TIME
Conditions
Temperature 76° F.
Relative Humidity 74%

| Paste Composition | Time Before Paste is Applied to Surface (Min.) | Setting Time (Min.) | Film Rating[a] | Working Time (Min.) |
|---|---|---|---|---|
| (PolyHEMA Powder:PEG-400) | | | | |
| 0.5:1.0 | 0 | >120 | Poor-tacky film, unable to remove | 0 |
|  | 5 | >120 | Poor-tacky film, unable to remove |  |
|  | 10 | >120 | Poor-tacky film, unable to remove |  |
|  | 20 | >120 | Poor-tacky film, unable to remove |  |
|  | 30 | >120 | Poor-tacky film, unable to remove |  |
|  | 60 | >120 | Poor-tacky film, unable to remove |  |
| 0.75:1.0 | 0 | >120 | Poor-tacky film, unable to remove | 0 |
|  | 10 | >120 | Poor-tacky film, unable to remove |  |
|  | 20 | >120 | Poor-tacky film, unable to remove |  |
|  | 30 | 69 | Poor |  |
|  | 40 | 45 | Poor |  |
|  | 50 | 35 | Poor |  |
| 0.85:1.0 | 0 | 59 | Excellent | 19–22 |
|  | 5 | 58 | Excellent |  |
|  | 9 | 57 | Excellent |  |
|  | 13 | 56 | Excellent |  |
|  | 16 | 55 | Excellent |  |
|  | 19 | 53 | Excellent |  |
|  | 22 | 53 | Poor |  |
|  | 24 | 52 | Poor |  |
|  | 27 | 50 | Poor |  |
| 1.0:1.0 | 0 | 54 | Excellent | 13–17 |
|  | 6.5 | 53.5 | Excellent |  |
|  | 10 | 52.5 | Excellent |  |
|  | 13 | 51 | Excellent |  |
|  | 17 | 49 | Good |  |
| 1.075:1.0 | 0 | 42 | Excellent | 10–13 |
|  | 5 | 38 | Excellent |  |
|  | 7.5 | 29.5 | Excellent |  |
|  | 10 | 34 | Excellent |  |
|  | 13 | 30 | Poor |  |
|  | 16 | 29 | Poor |  |
| 1.15:1.0 | 0 | 31 | Excellent | 9–12 |
|  | 4 | 31 | Excellent |  |
|  | 6.5 | 30.5 | Excellent |  |
|  | 9 | 30 | Excellent |  |
|  | 12 | 28 | Good |  |
| 1.25:1.0 | 0 | 25 | Excellent | up to 5 |
|  | 5 | 23 | Poor |  |
|  | 7.5 | 21.5 | Poor |  |
|  | 10 | 21 | Poor |  |
|  | 12 | 20 | Poor |  |
| 1.5:1.0 | Could not apply | | | |

[a] After flex test. Films prepared from polyHEMA powder:PEG-400 of 0.85 to 1.25:1 and rated "poor" after flex test were non-tacky, visually homogenous and occlusive films on the body surface (prior to flext test).

An effective burn dressing can be prepared in situ by the improved application method of premixing hydrophilic polymer and solvent at appropriate proportions and applying the resulting paste with a tongue depressor or other applicator. The qualities of the resulting film can be varied by varying the proportions of the polymer and liquid components. The setting time and working time of the novel pastes can be similarly varied. It is also apparent that the setting period is greater than the working time period. When the working time period was exceeded before application of the paste to the body surface, the resulting film or dressing received a "poor" rating after being subjected to the flex test. This poor rating indicates that the film speciment showed cracks or tears. However, these films (before removal from the body surface), at polymer:liquid ratios of approximately 0.85–1.40:1 by weight were characterized as non-tacky, visually homogeneous, occlusive films and, as such, are suitable for small wound dressings notwithstanding flex failure. On the other hand, application of the paste to the body surface within the working time period gave "excellent" films within the aforesaid range of ratios. For large severe body burns of the nature of second, third and fourth degree burns, formulations of approximately 1:1 to 1.2:1 (polymer:liquid) gives excellent working time and setting time periods which would enable hospital staff members to effectively treat the burn victim.

What is claimed is:

1. A process of treating a wound comprising applying to the surface of the wound a settable, non-toxic paste consisting essentially of a particulate, hydrophilic, water-swellable polymer and an inert, non-toxic water-miscible organic liquid having a boiling point above about 120° C. capable of forming a paste therewith, said organic liquid being polyethylene glycol or oxyethyleneoxypropylene glycol of 200–2000 molecular weight and said polymer being a polymer of hydroxy($C_2$–$C_4$-alkyl) methacrylate, hydroxy($C_2$–$C_4$alkyl) acrylate, hydroxy($C_2$–$C_4$alkoxy$C_2$–$C_4$alkyl)methacrylate, hydroxy($C_2$–$C_4$alkoxy$C_2$–$C_4$alkyl)acrylate, alkoxy($C_2$–$C_4$alkoxy$C_2$–$C_4$alkyl) methacrylate, alkoxy($C_2$–$C_4$alkoxy$C_2$–$C_4$alkyl) acrylate, N-($C_1$–$C_4$alkyl)acrylamide, N-($C_1$–$C_4$alkyl)methacrylamide, N,N-di($C_1$–$C_4$-alkyl)acrylamide, N,N-(di($C_1$–$C_4$alkyl)methacrylamide, vicinal-epoxy($C_1$–$C_4$alkyl methacrylate, or vicinal-epoxy($C_1$–$C_4$alkyl)acrylate, said paste having a setting time of up to about one hour and a working time sufficient to apply the paste to the said wound surface, the polymer of said paste in set condition being water-insoluble, the ratio of polymer to organic liquid in the paste being from above about 0.8:1 to about 1.4:1 by weight, whereby there is formed a non-tacky, homogeneous, occlusive film on the surface of the wound.

2. The process of claim 1 wherein the settable paste consists of the stated materials and a germicide, fungicide, antibiotic or analgesic.

3. The process of claim 1 wherein said paste is applied to a burned tissue surface.

4. The process of claim 1 wherein said paste has a working time less than about 45–50 minutes.

5. The process of claim 1 wherein said polymer is at least slightly crosslinked and has a molecular weight at least about 50,000.

6. The process of claim 5 wherein said organic liquid is characterized by a plurality of —$CH_2CH_2O$— units and a boiling point above about 200° C.

7. The process of claim 6 wherein said organic liquid is polyethylene glycol of 200–1600 molecular weight and said polymer is a polymer of hydroxy($C_2$–$C_4$-alkyl) methacrylate, hydroxy($C_2$–$C_4$alkyl) acrylate, hydroxy($C_2$–$C_4$alkoxy$C_2$–$C_4$alkyl)methacrylate, hydroxy($C_2$–$C_4$alkoxy-$C_2$–$C_4$alkyl)acrylate, alkoxy($C_2$–$C_4$alkyl)-methacrylate, alkoxy($C_2$–$C_4$alkoxy$C_2$–$C_4$alkyl) acrylate, N-($C_1$–$C_4$alkyl)acrylamide, N-($C_1$–$C_4$alkyl)methacrylamide, N,N-di($C_1$–$C_4$alkyl)acrylamide, N,N-(di(C-

1-C4alkyl)methacrylamide, vicinal-epoxy(C1-C4alkyl methacrylate, or vicinal-epoxy(C1-C4alkyl(acrylate.

8. The process of claim 7 wherein the polyethylene glycol has a molecular weight of 400-800.

9. The process of claim 7 wherein said polymer is characterized by at least 50 mol percent of the following recurring unit

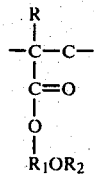

wherein R is hydrogen or methyl, wherein R1 is C2-C4alkylene, and wherein R2 is hydrogen, C1-C4alkyl or C1-C4alkoxyC1-C4alkyl.

10. The process of claim 9 wherein said polymer is characterized by at least 80 mol percent and wherein R is methyl and wherein R1 is C2-C4alkylene.

11. The process of claim 9 wherein said organic liquid is polyethylene glycol of 200-1000 molecular weight and wherein the polymer contains recurring 2-hydroxyethyl methacrylate units.

12. The process of claim 11 wherein said polymer is a crosslinked 2-hydroxyethyl methacrylate polymer.

13. The process of claim 12 wherein the ratio of polymer to organic liquid is from about 0.85:1 to below about 1.4:1 by weight.

14. The process of claim 13 wherein the ratio of polymer to organic liquid is from about 0.85:1 to about 1.25:1 by weight.

15. The process of claim 14 wherein said paste is applied to a burned tissue surface as a thin film and wherein the ratio of polymer to organic liquid is from approximately 1:1 to 1.2:1 by weight.

16. The process of claim 15 wherein the burned tissue surface is the surface of a second, third, or fourth degree burn.

17. The process of claim 13 wherein said paste contains a medicinally active ingredient therein.

18. A settable, non-toxic paste suitable for forming a homogeneous, non-tacky, non-toxic, occlusive film on the surface of a wound (1) said paste consisting essentially of (a) particulate water-insoluble, water-swellable, hydrophilic polymer and (b) an inert, water-miscible, organic liquid having a boiling point above about 120° C. and capable of forming a paste therewith, said organic liquid being polyethylene glycol or oxyethyleneoxypropylene glycol of 200-2000 molecular weight and said polymer being a polymer of hydroxy(C2-C4-alkyl) methacrylate, hydroxy(C2-C4alkyl) acrylate, hydroxy(C2-C4alkoxyC2-C4-alkyl)methacrylate, hydroxy(C2-C4alkoxyC2-C4alkyl)acrylate, alkoxy(C2-C4alkoxyC2-C4alkoxyC2-C4alkyl) methacrylate, alkoxy(C2-C4alkoxyC2-C4alkyl) acrylate, N-(C1-C4alkyl)acrylamide, N-(C1-C4alkyl)methacrylamide, N,N-di(C1-C4-alkyl)acrylamide, N,N-(di(C1-C4alkyl)-methacrylamide, vicinal-epoxy(C1-C4alkyl methacrylate, or vicinal-epoxy(C1-C4alkyl)acrylate; (2) said polymer being present in an amount sufficient to impart to said paste a setting time period no greater than about one hour and a working time sufficient to apply the paste to the wound surface; (3) the hydrophilic polymer of said paste in set condition remaining water-insoluble, the ratio of polymer to organic liquid in the paste being from above about 0.8:1 to about 1.4:1 by weight.

19. The settable paste of claim 18 wherein said polymer is at least slightly crosslinked and has a molecular weight at least about 50,000.

20. The settable paste of claim 19 wherein said organic liquid is characterized by a plurality of —CH2CH2O- units and a boiling point above about 200° C.

21. The settable paste of claim 20 wherein said organic liquid is polyethylene glycol of 200-1600 molecular weight and said polymer is a polymer of hydroxy(C2-C4-alkyl) methacrylate, hydroxy(C2-C4alkyl) acrylate, hydroxy(C2-C4alkoxyC2-C4alkyl) methacrylate, hydroxy(C2-C4alkoxyC2-C4alkyl) acrylate, alkoxy(C2-C4alkoxyC2-C4alkyl) methacrylate, alkoxy(C2-C4alkoxyC2-C4alkyl) acrylate, N-(C1-C4alkyl)acrylamide, N-(C1-C4alkyl)methacrylamide, N,N-di(C1-C4alkyl)acrylamide, N,N-di(C1-C4alkyl)methacrylamide, vicinal-epoxy(C1-C4alkyl) methacrylate, or vicinal-epoxy(C1-C4alkyl) acrylate.

22. The settable paste of claim 21 wherein said polymer is characterized by at least 50 mol percent of the following recurring unit

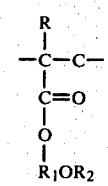

wherein R is hydrogen or methyl, wherein R1 is C2-C4alkylene, and wherein R2 is hydrogen, C1-C4alkyl or C1-C4alkoxy C1-C4alkyl.

23. The settable paste of claim 22 wherein said polymer is characterized by at least 80 mol percent and wherein R is methyl and wherein R1 is C2-C4alkylene.

24. The settable paste of claim 23 which is suitable for forming a homogeneous, integral, non-tacky, non-toxic, occlusive film on a burned tissue surface wherein said organic liquid is polyethylene glycol of 200-1000 molecular weight and wherein the polymer contains recurring 2-hydroxyethyl methacrylate units.

25. The settable paste of claim 24 wherein said polymer is a crosslinked 2-hydroxyethyl polymer and wherein the ratio of polymer to organic liquid in the paste is from above about 0.8:1 to about 1.4:1 by weight.

26. The settable paste of claim 25 wherein the ratio of polymer to organic liquid is from about 0.85:1 to below about 1.4:1 by weight.

27. The settable paste of claim 26 wherein the ratio of polymer to organic liquid is from about 0.85:1 to about 1.25:1 by weight.

28. The settable paste of claim 26 wherein said paste contains a medicinally active ingredient therein.

29. The settable paste of claim 27 wherein the molecular weight of the polyethylene glycol is 400-800.

30. The settable paste of claim 28 wherein the medicinally active ingredient is a germicide, fungicide, antibiotic or analgesic.

31. The settable paste of claim 30 wherein the medicinally active ingredient is an antibiotic.

32. The settable paste of claim 30 wherein the medicinally active ingredient is a germicide.

33. The settable paste of claim 30 wherein the medicinally active ingredient is a fungicide.

34. The settable paste of claim 30 wherein the medicinally active ingredient is an analgesic.

* * * * *